United States Patent
Ni et al.

(10) Patent No.: US 6,274,548 B1
(45) Date of Patent: Aug. 14, 2001

(54) PECTIC SUBSTANCE AS A GROWTH FACTOR STABILIZER

(75) Inventors: Yawei Ni, College Station; Kenneth M. Yates, Grand Prairie, both of TX (US)

(73) Assignee: Carrington Laboratories, Inc., Irving, TX (US)

( * ) Notice: Subject to any disclaimer, the term of this patent is extended or adjusted under 35 U.S.C. 154(b) by 0 days.

(21) Appl. No.: 09/325,923

(22) Filed: Jun. 4, 1999

Related U.S. Application Data (60) Division of application No. 09/122,010, filed on Jul. 24, 1998, and a continuation-in-part of application No. 09/078,204, filed on May 13, 1998.

(51) Int. Cl.[7] .................................................. A61K 37/00
(52) U.S. Cl. ................................ 514/2; 514/2; 514/12; 514/14; 514/54; 530/350; 530/399; 536/2
(58) Field of Search .................. 514/2, 12, 14, 514/54; 530/350, 399; 536/2

(56) References Cited

U.S. PATENT DOCUMENTS

| | | | |
|---|---|---|---|
| 5,122,597 | 6/1992 | Barritault et al. ..................... | 530/399 |
| 5,130,418 | 7/1992 | Thompson ............................ | 530/399 |
| 5,191,067 | 3/1993 | Lappi et al. ......................... | 530/399 |
| 5,217,954 | 6/1993 | Foster et al. ........................ | 514/12 |
| 5,310,883 | 5/1994 | Seddon et al. ....................... | 530/399 |
| 5,356,630 | 10/1994 | Laurencin et al. .................... | 424/426 |
| 5,409,703 | * 4/1995 | McAnalley et al. ................. | 424/435 |
| 5,422,340 | 6/1995 | Ammann et al. ....................... | 514/12 |

(List continued on next page.)

FOREIGN PATENT DOCUMENTS

| 97/03574 | * 2/1997 | (WO) . |
|---|---|---|
| 00/05257 | * 2/2000 | (WO) . |

OTHER PUBLICATIONS

Penel et al. "Pectin binding proteins: Characterization of the binding and comparison with heparin", Plant Physiol. Biochem., vol. 34(4): 479–488.*

Gauhari Mandal and Amalendu Das, "Structure of the dGalactan Isolated from aloe Barbadensis Miller."Carbohydrate Research. vol. 86, 1980. pp. 247–257.

R.G. Ovodova, V.F. Lapchik and Yu S. Ovodov, "Polysaccharides of Aloe Arborescens, "Plenum Publishing Corporation, 1976, pp. 1–2.

Gauhari Mandal, Rina Ghosh and Amalendu Das, "Characterisation of Polysaccharides of Aloe Bardadensis Miller: Part III –Structure of an acidic Oligosaccharide, "Indian Journal of Chemistry, vol. 22B, Sep. 1983. pp. 890–893.

(List continued on next page.)

*Primary Examiner*—Ralph Gitomer
*Assistant Examiner*—D. Khare
(74) *Attorney, Agent, or Firm*—Jackson Walker L.L.P.

(57) ABSTRACT

Pectic substance from Aloe Vera and other sources is used as a stabilizer and a delivery vehicle for pectin/heparin-binding proteins, such as pectin/heparin binding growth factors. Aloe pectin, a naturally occurring LM (low methoxyl) pectin, binds to pectin/heparin-binding growth factors, i.e., bFGF, aFGF, and KGF of fibroblast growth factor (FGF) family and TGF-β1 of transforming growth factor-β (TGF-β) family. Commercial LM or HM (high methoxyl) citrus pectins tested did not exhibit any binding activity with bFGF. A weak binding to bFGF was observed with a de-esterified pectin (polygalacturonic acid) prepared from citrus. The binding protected the growth factor from protease digestion. The calcium gel beads prepared with Aloe pectin also bound to these pectin/heparin-binding growth factors. The growth factor could also be encapsulated in the pectin calcium gel and Aloe pectin sodium gel. Pectin/heparin-binding growth factor stabilized by pectin is used for wound healing. A pectin-containing matrix is used for the isolation of a pectin/heparin-binding protein.

4 Claims, 5 Drawing Sheets

U.S. PATENT DOCUMENTS

| | | | |
|---|---|---|---|
| 5,441,943 | * 8/1995 | McAnalley et al. | 514/54 |
| 5,453,492 | 9/1995 | Butzow et al. | 530/413 |
| 5,464,815 | 11/1995 | Chamow et al. | 514/8 |
| 5,514,652 | 5/1996 | Watanuki et al. | 514/12 |
| 5,552,528 | 9/1996 | Burgess et al. | 530/399 |
| 5,576,288 | 11/1996 | Lappi et al. | 514/2 |
| 5,589,451 | 12/1996 | Wilson | 512/2 |
| 5,604,204 | 2/1997 | Ammann et al. | 514/12 |
| 5,612,211 | 3/1997 | Wilson et al. | 435/378 |
| 5,614,496 | 3/1997 | Dunstan et al. | 514/12 |
| 5,654,312 | * 8/1997 | Andrulis et al. | 514/279 |
| 5,656,587 | 8/1997 | Sporn et al. | 514/2 |
| 5,656,598 | 8/1997 | Dunstan et al. | 514/12 |
| 5,665,870 | 9/1997 | Rubin et al. | 530/412 |
| 5,693,775 | 12/1997 | Nathans et al. | 536/23.1 |
| 5,703,047 | 12/1997 | Wilson | 514/12 |
| 5,714,458 | 2/1998 | Adami et al. | 514/2 |
| 5,753,622 | 5/1998 | Buret et al. | 514/12 |
| 5,929,051 | * 7/1999 | Ni et al. | 514/54 |

OTHER PUBLICATIONS

A.G.J. Voragen, W. Pilnik, Jean–Francois Thibault, M.A.V. Axelos, and Catherine M.G.C. Renard. "Pectins" in Food Polysaccharides and their applications. A.M. Stephen., Ed., Chp. 10, pp. 287–339. Marcel Dekker (1995).

Alan D. Cardin and H.J.R. Weintraub, "Moleculat Modeling of Protein–Glycosaminoglycan Interactions,"1987 American Heart Associattion Meeting, pp. 21–32.

Joseph Schlessinger, Irit Lax and Mark Lemmon. "Regulation of Growth Factor Activation by Proteoglycans: What is the Tole of the Low Affinity Receptors?, " Cell, vol. 83, Nov. 3, 1995, pp. 357–360.

H. Edward Conrad, "Heparin–Binding Proteins –Chp. 1. Heparin vs. Heparan Sulfate, " Academic Press, 1998, pp. 1–5.

H. Edward Conrad, "Heparin–Binding Proteins –Chp. 6. Heparinoid/Protein Interactions, " Academic Press, 1998, pp. 183–202.

H. Edward Conrad, "Heparin–Binding Proteins –Chp. 9 fibroblast growth factors, "Academic Press, 1998, pp. 301–349.

James N . BeMiller, "An Introduction to Pectins: Structure and Properties, " 189th Meeting of the American Chemical Society, Apr. 28–May 3, 1985, pp. 1–12.

Farhad Radiabi, Claudine Amar and Erna Vilkas, "Structural Studies of the Glucomannan from Aloe Vahombe, " Carbohydrate Research, 1983, pp. 166–170.

T. P. Kravtchenko, I. Arnould, A.G.J. Voragen & W. Pilnik, "Improvement of the Selective Depolymerization of Pectin Substances by Chemical β–Elimination in Aqueous Solution, " Carbohydrate Polymers 19, 1992, pp. 237–242.

Catherine M.G.C. Renard and Jean–Francois Thibault, "Structure and Properties of Apple and Sugar–Beet Pectins Extracted by Chelating Agents, "Carbohydrate Research 244, 1993, pp. 99–114.

Colin D. May, "Industrial Pectins: Sources, Production and Applications, "Carbohydrate Polymers 12, 1990, pp. 79–99.

R.R. Selevendran, B.J.H. Stevens, M.A. O'Neill, Developments in the Isolation and Analysis of Cell Walls from Edible Plants, Biochemistry of Plant Cell Walls, pp. 39–79.

Wilfred T. Mabusela et al.: "Carbohydrate Polymers from Aloe Ferox Leaves"Phytochemistry, vol. 29, no. 11, 1990, pp. 3555–3558, XP002111912 Great Britain.

* cited by examiner

PECTIC SUBSTANCE AS A GROWTH FACTOR STABILIZER

This is a divisional of U.S. patent application Ser. No. 09/122,010, filed on Jul. 24, 1998 continuation-in-part of U.S. patent application Ser. No. 09/078,204, filed May 13, 1998.

BACKGROUND

This invention relates to using a pectic substance to stabilize a pectin/heparin-binding protein, the resultant composition and formulation, and the method of stabilizing the pectin/heparin-binding protein.

Following abbreviations are used in this invention:

aFGF, acidic fibroblast growth factor, bFGF, basic fibroblast growth factor, BSA, bovine serum albumin; Da, dalton; DAc, degree of acetylation; DM, degree of methylation; EDTA, ethylenediaminetetraacetic acid; EGF, epidermal growth factor, Gal A, galacturonic acid; EN, high methoxyl; HMw, high-molecular-weight; IL, interleukin, kDa, kilodalton; KGF, keratinocyte growth factor, LM low methoxyl; LMW, low-molecular-weight; PDGF, platelet-derived growth factor; SDS, sodium dodecyl sulfate; TGF-$\alpha$, transforming growth factor-$\alpha$; TGF-$\beta$1, transforming growth factor-$\beta$1; TN buffer, 25 mM Tris, 0.15 M NaCl, pH 7.4; TNF-$\alpha$, tumor necrosis factor-$\alpha$.

Pectin is a plant cell wall component. The cell wall is divided into three layers, middle lamella, primary, and secondary cell wall. The middle lamella is the richest in pectin. Pectins are produced and deposited during cell wall growth and are particularly abundant in soft plant tissues under conditions of fast growth and high moisture content. In cell walls pectins are present in the form of a calcium complex. The involvement of calcium cross-linking is substantiated by the fact that chelating agents facilitate the release of pectin from cell walls.

Pectin is a complex polysaccharide. It consists of an $\alpha$1–4 linked polygalacturonic acid backbone intervened by rhamnose residues and modified with neutral sugar side chains and non-sugar components such as acetyl, methyl and ferulic acid groups. The neutral sugar side chains which include arabinan and arabinogalactans (Types I and II) are attached to the rhamnose residues in the backbone at the O-3 or O-4 position. The rhamnose residues tend to cluster together on the backbone. So with the side chains attached this region is referred as the hairy region and the rest of the backbone is hence named the smooth region. Rhamnose residues are 1–2 linked to Gal A residues in the backbone and the configuration of this linkage has now been determined to be $\alpha$.

Because of the presence of neutral sugar side chains and some other non-sugar components, the structure of pectins is very complex; essentially no two molecules have identical structures.

Rhamnose, galactose, arabinose, and xylose are the most common neutral sugar components of pectins. The less common ones are glucose, mannose, and fucose. Some of the xylose residues are individually attached to Gal A residues at the O-3 position. Three types of neutral sugar side chains have been identified in pectins. Arabinan consists of $\alpha$1-5 linked arabinose. Arabinogalactans I consists of $\beta$1–4 linked galactose with short arabinan chains attached at O-3. In arabinogalactan II, galactose is $\beta$1–3&6 linked with arabinose attached.

Methylation occurs at carboxyl groups of Gal A residues. The degree of methyl-esterification is defined as the percentage of carboxyl groups (Gal A residues) esterified with methanol. A pectin with a degree of methylation ("DM") above 50% is considered a high methoxyl ("HM") pectin and one with a DM<50% is referred to as low methoxyl ("LM") pectin. Most of the natural pectins are HM with a few exceptions such as sunflower pectin. The degree of acetylation (DAc) is defined as the percentage of Gal A residues esterified with one acetyl group. It is assumed that only the hydroxyl groups are acetylated. Since each Gal A residue has more than one hydroxyl group, the DAc can be above 100%. DAc is generally low in native pectins except for some such as sugar beet pectin.

Generally, pectins are soluble in water and insoluble in most organic solvents. Pectins with a very low level of methyl-esterification and pectic acids are only soluble as the potassium or sodium salts. As for other polymers, there is no saturation limit for pectins, but it is difficult to obtain a true solution with concentrations higher than 3–4%. Commercial pectins have a size range of 7–14×$10^4$ Da with citrus pectins being larger than apple pectins. Viscosities of pectin solutions are generally low and so pectins are seldom used as thickening agents. The viscosity is directly related to the size, pH, and also to the presence of counterions. Addition of monovalent cations reduces viscosity.

The Gal A residues in the pectin backbone are $\alpha$1–4 linked. Both hydroxyl groups of Gal A at carbon atoms 1 and 4 are in the anal position. The resulting linkage is therefore trans 1–4. This type of linkage results in increased chain stiffness of the polymer. So pectin with a flexibility parameter B between 0.072–0.017 are rigid molecules. It has been suggested that the insertion of rhamnose residues in the backbone cause a T-shaped kink in the backbone chain. An increase in rhamnose content leads to more flexible molecules. Pectins can be considered as a zigzag polymer with long and rigid smooth regions and flexible hairy regions (rich in rhamnose) serving as rotating joints. The DM also has certain effects on chain flexibility. In solution, pectin molecules have been shown to assume a right-handed helical structure.

Pectins are most stable at pH 3–4. Below pH 3, methoxyl and acetyl groups and neutral sugar side chains are removed. At elevated temperatures, these reactions are accelerated and cleavage of glycosidic bonds in the galacturonan backbone occurs. Under neutral and alkaline conditions, methyl ester groups are saponified and the polygalacturonan backbone breaks through $\beta$-elimination-cleavage of glycosidic bonds at the non-reducing ends of methoxylated galacturonic acid residues. These reactions also proceed faster with increasing temperature. Pectic acids and LM pectins are resistant to neutral and alkaline conditions since there are no or only limited numbers of methyl ester groups.

Both HM and LM pectins can form gels, but by totally different mechanisms. HM pectins form gels in the presence of high concentrations of co-solutes (sucrose) at low pH. LM pectins form gels in the presence of calcium In addition, the sugar beet pectin can form gels through cross-linking of the ferulated groups.

The calcium-LM pectin gel network is built by formation of the "egg-box" junction zones in which Ca++ ions cause the cross-linking of two stretches of polygalacturonic acids. In apple and citrus pectins, stretches of polygalacturonic acids without rhamnose insertion have been estimated to be as long as 72–100 residues. The zone is terminated by the rhamnose residue in the backbone. The calcium-LM pectin gel is thermoreversible. The calcium can therefore be added at the boiling point and gel formation occurs upon cooling. It is possible to obtain a firm resilient gel with 0.5% pectin and 30–60 mg/g Ca++. A high content of pectin with little calcium gives an elastic gel; whereas, a high calcium concentration with a minimum of pectin results in a brittle gel.

Industrial pectins, either HM or LM are mainly obtained from apple and citrus by acid extraction and alcohol precipitation. LM pectins are obtained from HM ones by chemical de-esterification. Pectins have a favorable regulatory status as a food additive. They are classified as Generally Recognized As Safe ("GRAS") in the United States and Acceptable Daily Intake ("ADI") in Europe. That is, its use is only limited by current Good Manufacturing Practice ("cGMP") requirements to meet certain specifications. These specifications include a minimal Gal A content of 65% (w/w).

Many other plant sources have also been examined for pectin production. Two of them, sugar beet pulp and sunflower head, have been studied extensively. Both are abundant as raw materials. However, sugar beet pectin has a poor gel forming ability largely due to its high acetyl group content and small molecular size ($\sim 5 \times 10^4$ Da). The sunflower pectins are naturally LM and can be efficiently extracted with chelating agents. Chemically, sunflower head pectin has a very high Gal A content and is a natural LM pectin, whereas sugar beet pectin has a relatively low Gal A content and a very high content of acetyl and ferulic acid groups. The structures of apple and citrus pectins are very similar to each other. Pectins are traditionally used as food additives. However, their use has extended into pharmaceutical areas as well. They often suffer from poor quality of raw materials and poor color quality (usually tan) of the pectin end products.

Pectins from different plant sources have different characteristics. In general, all commercial pectins including those that have gone through further processing have a certain degree of coloration as a final product. The color ranges from light yellow/brown (citrus pectin) to dark tan (apple and sunflower head pectins). The coloration is caused by the combination of two factors: natural color (pigmentation) of the raw materials and their content of polyphenols.

Pectins are effective against gastrointestinal ulcers and enterocolitica. Pectins also influence cell proliferation in the intestines. They also have a blood cholesterol-lowering effect and exhibit inhibition of antherosclerosis. This effect is the result of interactions between pectins and bile salts. Pectins have also been shown to affect the fibrin network in hypercholesterolaemic individuals. Pectins are also effective in removing lead and mercury from the digestive tract and respiratory organs.

Proteins possess unique chemical and physical properties which pose difficult stability problems: a variety of degradation pathways exist of proteins, involving both chemical and physical instability. These macromolecules are also at risk from microbial degradation due to adventitious contamination of the solutions during purification or storage. All these considerations are especially critical for the pharmaceutical manufacturer who is formulating and packaging these agents. Thus, a thorough pre-formulation program is an essential step for protein drugs, to solve their possible formulation problems.

SUMMARY

The present invention relates to composition and method of manufacture of a stabilized pectin/heparin-binding protein having a pectin/heparin-binding protein and a pectic substance in an amount effective to stabilize the pectin/heparin-binding protein. Useful pectin/heparin-binding protein includes pectin/heparin-binding growth factors. Useful pectic substance includes Aloe pectin, low methoxyl pectin, de-esterified pectin, pectic acid, pectate, pectinic acid, pectinate, pectin calcium gel, Aloe pectin sodium gel, Aloe Vera inner gel cell wall fiber, and others.

In one embodiment, the present invention provides a pharmaceutical formulation which comprises a pectic substance, a pectin/heparin-binding growth factor and a thickener.

In another embodiment, the present invention provides a method of isolating a pectin/heparin-binding protein.

BRIEF DESCRIPTION OF THE DRAWINGS

FIGS. 1a–bshow the binding of Aloe pectin to bFGF. The binding assay was carried out with pectin-rich Aloe Vera inner gel cell wall fibers as described in Example 6. Soluble Aloe pectin (FIGS. 1a and 1b) or heparin (FIG. 1b) was used as the inhibitor. A sample of bFGF (0.5 µg) was directly loaded onto the gel as a standard for comparison of the OD values (FIG. 1a), which was not a part of the binding or inhibition reaction as indicated by "x."

DETAILED DESCRIPTION

Thus, the general term "pectic substance," as used in this invention, includes pectin, low methoxyl pectin, de-esterified pectin, pectin calcium gel, Aloe pectin sodium gel, pectic acid, pectate, pectinic acid, pectinate, protopectin, and pectin-rich substances, such as Aloe Vera inner gel cell wall fiber, individually, collectively, or in combination thereof As discussed above, pectin is a group designation for those complex colloidal carbohydrate derivatives which occur in, or are prepared from, plants and contain a large proportion of anhydrogalacturonic acid units which are thought to exist in a chain-like combination. The carboxyl groups may be partially esterified by methyl groups and partially or completely neutralized by one or more bases. Thus, "de-esterified" usually means that one or more methyl ester groups have been removed from the pectin molecules. "Pectic acids" is the group designation applied to pectic substances mostly composed of colloidal polygalacturonic acids and essentially free from methyl ester groups. The totally de-esterified pectin is pectic acid or polygalacturonic acid. "Pectates" are either normal or acid salts of pectic acids. "Pectinic acids" are the colloidal polygalacturonic acids containing more than a negligible proportion of methyl ester groups. "Pectinates" are either normal or acid salts of pectinic acids. "Protopectin" is applied to the water-insoluble parent pectin which occurs in plants and which upon restricted hydrolysis yields pectins, pectinic acids, and others. The water-insoluble pectin may be associated with the cellulose present in the plant, such as the Aloe Vera inner gel call wall fiber.

Aloe Pectin

Aloe Vera leaves consist of two parts, an outer green rind and a clear inner gel which is also referred as pulp. Aloe pectin is extracted from the inner gel or outer rind cell wall fibers. Use of a chelating agent at a slight alkaline pH is found to be the most efficient extraction method. Aloe pectin is unique as compared to previously described pectins. It has a high rhamonse content, >4% in the purified pectin preparation which is at least 2 times higher than in other pectins such as citrus, apple, sugar beet, and sunflower. Rhamnose is a key sugar in the pectin backbone whose content affects the flexibility of the molecule. Aloe pectin also possesses a rare sugar, 3-OMe-rhamnose which has not been described in any other pectins. Aloe pectin is naturally LM, having a DM generally <30% and often <10%. The Gal A content of Aloe pectin is >70%. Aloe pectin is capable of gel formation in the presence of calcium. Uniquely, Aloe pectin, especially the high-molecular-weight (HMW) one, can also form a monovalent cation-based reversible gel at low temperature (4° C.) at a pectin concentration as low as 1 mg/ml. An example of the monovalent cation is sodium. Such cold gelation has not been described for any other pectins.

Aloe pectin extracted from the inner gel fibers is an off white powder and produces a clear solution as compared to the yellow to tan powders and cloudy solutions of current commercial and experimental pectins from citrus, apple, sugar beet, or sunflower.

Aloe pectin can be distinguished from other pectins by one or more of the following characteristics:

1) A high molecular weight ($>1 \times 10^6$ Da) and a high intrinsic viscosity (>550 ml/g).
2) A high rhamnose content (>4%).
3) Containing 3-OMe-rhamnose.
4) Being naturally LM.
5) Capable of calcium gel formation.
6) Capable of monovalent cation-based gel formation at low temperature (4° C.).
7) Off white powder and clear solution (Aloe pectin extracted from inner gel fibers).

Pectin/Heparin-Binding Proteins

In the mammalian system, there are over 100 heparin-binding proteins. These include: (1) cellular matrix proteins, such as collagen, fibronectin, and vitronectin; (2) cytokines such as IL-3, IL-8, IFN-γ, PF4, MIP-1, and members of fibroblast growth factor and transforming growth factor-β families; (3) enzymes such as elastase and phospholipase A2; (4) proteins involved in blood clotting such as antithrombin, thrombin, and fibrin; and others.

There is a large number of cytokines that are essential regulators of various biological functions in a mammal. They are usually low-molecular-weight proteins or peptides. Some of these cytokines are growth factors. Growth factors are proteins or peptides that are capable of stimulating cell division. They are important factors in cell proliferation and development. There are five major growth factor families, epidermal growth factor (EGF), transforming growth factor-β (TGF-β), platelet-derived growth factor (PDGF), insulin-like growth factor (IGF), and fibroblast growth factor (FGF). Growth factors also are important in wound healing. bFGF and TGF-β have been widely studied for accelerating wound healing. As used in this invention, the term "growth factor" denotes a natural and/or a recombinant growth factor, purified or unpurified, in vitro, in vivo, or ex vivo.

Many growth factors are heparin-binding, including members of the TGF-β and FGF families. This binding is crucial for their functions. Heparin is a polymer of a sulfated disaccharide repeat sequence ($\rightarrow$GlcAβ1-4GlcNAcα1) (Casu, (1989), *Annals of New York Academy of Science* 556, pp. 1–17). It is derived from the polysaccharide chains of proteoglycans commonly found on cell surfaces, i.e., glycosaminoglycan (GAG). Like pectin, heparin is a negatively charged molecule. The interaction of heparin with heparin-binding proteins, including acidic or basic fibroblast growth factor (aFGF or bFGF), has been extensively studied. The heparin-binding domains on aFGF and bFGF have been identified. Such domains always involve positively charged amino acid residues, which play a major role in mediating the binding to the heparin through ionic interaction (Cardin and Weintraub, (1988), *Arteriosclerosis* 9, pp.21–32; Faham et aln, (1996), *Science* 271, pp. 1116–1120). The minimal binding site on heparin for some of these growth factors has also been identified The one for bFGF has been shown to consist of only five or six sugars. Due to variation in the extent and position of sulfation, the protein binding specificities may be different among different regions of a single heparin molecule. That is, different heparin-binding proteins may bind to different regions of heparin molecules.

The binding to heparin stabilizes growth factors against inactivation by heat acid, and protease digestion and provides a growth factor reservoir and a bioavailability control mechanism. The heparin-binding also facilitates the binding of growth factors to their high-affinity signaling receptors and induction of the cross-linking of the receptors for initiating signal transduction.

Aloe Vera inner gel, a water storage tissue, consists of large mesophyll cells that contain only a very limited number of degenerated cellular organelles. Following disruption of the inner gel by homogenization, mesophyll cell wall fibers (broken mesophyll cell wall fragments) can be isolated by low-speed centrifugation or filtration. These fibers appear to be clear transparent sheets under microscope. They are rich in Aloe pectin (50%, w/w) which can be extracted or solubilized with the chelating agent EDTA.

The inner gel cell wall fibers could be readily pelleted by low-speed centrifugation. Thus, binding assays for determining if Aloe pectin binds to any growth factors, cytokines, or other proteins could be performed using these fibers. The actual binding to Aloe pectin was confirmed by an inhibition assay using the soluble Aloe pectin. The results showed that Aloe pectin bound to heparin-binding growth factors, atGF, bFGF, KGF of FGF family, and TGF-β1 of TGF-β family, but not to any non-heparin-binding proteins tested. The binding to heparin-binding proteins, however, was selective since Aloe pectin did not bind to several other heparin-binding proteins tested. The binding was inhibited by soluble Aloe pectin, thus confirming that the binding to the pectin-rich cell wall fibers was actually mediated by the pectin molecules. The binding was also inhibited by heparin, being consistent with the heparin-binding nature of these growth factors. The commercial LM or HM pectins tested did not exhibit any binding activity as shown with bFGF. However, a weak binding to bFGF was observed with a de-esterified citrus pectin (i.e. polygalacturonic acid).

The binding protected the growth factor from protease digestion as demonstrated with bFGF. Both soluble Aloe pectin and pectin-rich inner gel cell wall fibers exhibited the protection effect. A protection effect, although weaker, was also observed with the polygalacturonic acid from citrus. This indicates that pectin can be used as a stabilizer for these pectin/heparin-binding growth factors. As used in this invention, a heparin-binding proteins that also binds to a pectin is termed "pectin/heparin-binding protein." Thus, a "pectin/heparin-binding growth factor" is a growth factor that binds to a heparin and also binds to a pectin. The calcium gel beads prepared with Aloe pectin also bound to these pectin/heparin-binding growth factors. Thus, the pre-formed pectin beads can be loaded with such growth factors for delivery purposes. In addition, the growth factors could also be encapsulated in the pectin calcium gel bead for delivery purpose. Furthermore these growth factors can also be entrapped in the monovalent cation-based gel as a storage from, which has an added advantage of preventing aggregate formation and permitting the eventual use in a solution for m. Thus, pectin can be used in various forms for stabilization and delivery of pectin/heparin-binding growth factors, i.e., a solution, a pre-formed calcium gel, a calcium gel formed in the presence of the growth factor, and a monovalent cation-based gel formed in the presence of the growth factor. Lastly, the pectin-rich inner gel fiber can also be used as a stabilizer for the pectin/heparin-binding growth factors.

The binding strength of these growth factors to Aloe pectin was assessed by affinity chromatography using inner gel cell wall fiber as a pectin-containing matrix and bFGF as the binding ligand. The results showed that the binding strength to Aloe pectin was moderate (0.5–0.7 M NaCl) and weaker than that (1.4–1.6 M NaCl for bFGF) to heparin (0.3–0.4 M NaCl is considered weak binding and >1.0 M NaCl is considered strong binding; Conrade, (1998), Heparin-binding Proteins, Academic Press, San Diego, pp. 197–199). The weaker affinity to Aloe pectin most likely makes it even more suitable for using Aloe pectin as a stabilizer and delivery vehicle; once the growth factor in complex with pectin makes contact with the glycosaminoglycan (heparin) on the cell surface, it will bind to the latter, its natural higher-affinity ligand, to initiate a stimulatory effect on the cells.

TABLE 1

Interaction of Aloe pectin with heparin-binding growth factors.

| | Proteins | Binding to Aloe pectin |
|---|---|---|
| Heparin-binding | bFGF | Yes |
| | aFGF | Yes |
| | KGF | Yes |
| | TGF-$\beta$ | Yes |
| | Fibronectin | No |
| | IL-8 | No |
| | IFN-$\gamma$ | No |
| Non-heparin-binding | TGF-$\alpha$ | No |
| | PDGF | No |
| | TNF-$\alpha$ | No |
| | EGF | No |
| | IL-1$\beta$ | No |
| | Complement C3 | No |
| | BSA | No |

Materials

Aloe Vera (Aloe Barberdensis Miller) plants (10") were obtained from H&P sales, Inc (Vista, Calif.) through Lowe's store. Bulk acetylated mannan ("BAM" also known as acemarnan hydrogel) is an Aloe Vera inner gel extract of Carrington Laboratories, Inc. Various commercial pectins and polygalacturonic acid were used. They include HM citrus (P-9561 with a DM of 92% and P-9436 with a DM of 64%), LM citrus (P-9311 with a DM of 28%), polygalacturonic acid (P-1879) from Sigma Chemical Co., HM citrus (PE100 with a DM of 67%) from Spectrum Chemical Co., and HM citrus (CU401) and apple (AU201) from Herbstreith-Fox KG. Following reagents were also obtained from Sigma Chemical Co.; disodium EDTA, tetrasodium EDTA, endo-polygalacturonase, and all neutral and acidic sugars used. The alkaline phosphatase substrate pNPP was obtained from Pierce. Sodium hexametaphosphate was obtained from Fluka Cherie AG.

Recombinant growth factors/cytokines aFGF (acidic fibroblast growth factor), bFGF (basic fibroblast growth factor), KGF (keratinocyte growth factor), EGF (epidermal growth factor), TGF-$\alpha$ (transforming growth factor-$\alpha$), TNF-$\alpha$ (tumor necrosis factor-$\alpha$), and IL-8 (interleukin-8) were obtained from Promega (Madison, Wis.). Recombinant TGF-$\beta$1 (transforming growth factor-$\beta$1), IFN-$\gamma$ (interferon-$\gamma$), PDGF (platelet-derived growth factor), and IL-1$\beta$ (interleukin-1$\beta$) were obtained from R&D systems Minneapolis, Minn.) Fibronectin was obtained from Gibco-BRL. Complement C3, bovine serum albumin (BSA), and heparin were obtained from Sigma Chemical Co (St. Louis, Mo.) All the proteins were of human origin except for TGF-$\beta$1 which is of porcine orgn.

Generally, BAM may be prepared from Aloe leaves as follows:

1. Aloe leaves are washed, sliced open and filleted to remove the leaf rind. The clean (substantially anthraquinones free) inner gel is retained while the green rind is discarded.

2. The filleted material is homogenized (creparo) and extensively filtered with a Finisher Model 75 (FMC, Chicago, Ill.) to remove most of the fiber.

3. The clear viscous gel is acidified to a pH of approximately 3.2 with dilute HCl.

4. The acidified gel is then extracted with four volumes of 95 % ethanol at ambient temperature. Floating material is removed, then the alcohol/water mixture is siphoned off while the solid precipitate is collected by centrifugation. Most alcohol/water soluble substances such as organic acids, oligosaccharides, monosaccharides, anthraquinones and inorganic salts are eliminated by the alcohol extraction process.

5. The solid Aloe Vera extract is then washed with fresh alcohol, centrifuged, freeze dried, and ground to a white powder.

The product is stable at room temperature in the freeze-dried form for several years if protected from additional moisture. The detailed procedures for producing substantially anthraquinone-free Aloe gel, for producing substantially anthraquinone-free Aloe juice, for extracting active chemical substance(s) from an Aloe leaf, for preparing BAM and for extracting from an Aloe leaf substantially non-degradable lyophilized ordered linear polymers of mannose have been described in Carrington's U.S. Pat. Nos. 4,735, 935, 4,851,224, 4,917,890, 4,957,907, 4,959,214, and 4,966, 892, the entire content of each of which is incorporated by reference. The uses of Aloe products have been described in Carrington's U.S. Pat. Nos. 5,106,616, 5,118,673, 5,308, 838, 5,409,703, 5,441,943, and 5,443,830, the entire content of each of which is hereby incorporated by reference.

A dispersant (or a protective colloid, a suspending agent, a stabilizer, or an emulsifier) can be selected from a wide variety of materials. Non-limiting examples include glycerine, a polyvinylpyrrolidone ("PVP"), or a PVP K homopolymer, such as: PVP K-15 powder having an average molecular weight ("Mv") of 8000 Daltons; PVP K-30 powder, Mv 38,000 Daltons; PVP K-60, 45% solution, Mv 216,000 Daltons; PVP K-90 powder, Mv 630,000 Daltons; or PVP K-120 powder, Mv 2,900,000 Daltons. Other dispersants include a series of vinylpyrrolidone ("VP")/vinyl acetate ("VA") copolymers, which copolymers covering a range of VP/VA mole ratios [given in bracket], supplied as either ethanol solution ("E"), isopropanol solution ("F"), or solid ("S"), PVP/VA E-735 [70/30], PVP/VA E-635 [60/40], PVP/VA E-535 [50/50], PVP/VAE-335 [30/70], the corresponding isopropanol solution and PVP/VAI-235 [20/80], PVP/VA S-630 [60/40]. Other dispersants include: Polyvinylpyrrolidone, pharmaceutical grade, known as Povidone USP or Polyvidonum, some of which are supplied as Plasdore C-15, Plasdore C-30 Plasdone K-25, Plasdone K-25, Plasdone K-26/28. Plasdone K-29/32. Plasdone K-90, or Plasdone K-120. Another class of dispersant is Crospovidone NF Polyvidonum insoluble, crosslinked N-vinyl-2-pyrrolidone. Still other dispersant includes: Poly(methyl vinyl ether/maleic anhydride) (linear interpolymer with 1:1 molar ratio) Series of copolymers, supplied as Gantrez® AN-119, having molecular weight as determined by membrane osmometry ("M.Wt.") of 20,000, Gantrez® AN-139 M.Wt. 41,000, Gantrez® AN-149 M.Wt. 50,000, and Gantrez® AN-169 M.Wt. 67,000

The dispersant is sometimes termed a protective colloid, a suspending agent, or an emulsifier.

Exemplary thickeners useful in this invention include: Those which are organic in nature (such as karaya gum, acacia gum, tragacanth, methylcellulose, hydroxymethylcellulose, and sodium carboxymethylcellulose) or synthetic polymers (such as polyethylene oxide, vinyl methyl ether/maleic anhydride compounds, cationic polyacrylamide compounds, or acetic polyvinyl). Many of these are largely carbohydrates or carbohydrate-like and swell with the addition of water. Preferably the thickeners are hydroxyethylcelluloses, such as Natrosol H (38000 cp), Natrosol 250 G Pharm (150–200 cp), and Natrosol 250 GL (75–150 cp).

The invention will be more fully understood by reference to the following examples. They should not, however, be construed as limiting the scope of the invention. All literature citations are incorporated by reference.

EXAMPLE 1

Extraction of Aloe Pectins
Preparation of Cell Wall Fibers

Two types of cell wail fibers were used, alcohol-treated and non-alcohol-treated The alcohol-treated fibers were isolated from BAM by centrifugation. BAM was dissolved in water at 2 mg/ml. The solution was then centrifuged at 180 g for 10 min. The pellet consisting of cell wall fibers, was harvested and washed three times with water before being dried. Since BAM has gone through alcohol precipitation, these fibers are therefore similar to those alcohol insoluble residues or solids (AIS) that are commonly prepared for extraction of pectins from other plant tissues.

The non-alcohol-treated fibers include the crude pulp and rind fibers. Crude pulp fibers were those retained by the coarse filtration during production of BAM and other pulp-based products. They are the same as those found in BAM, except for being larger in size and not alcohol-treated. They were collected with a no. 18 sieve (1 mm opening) with minimal loss and washed three times with water. The green rind, accounting for ~60% wet weight of the whole leaf, are generally discarded as waste by manufacturers. It contained the green rind proper as well as some pulp left behind -after filleting. The fibers were isolated from them in a similar way to those from pulp following homogenization. They were washed extensively, at least three times, with water, then dried and stored at room temperature ("RT") before being used for pectin extraction.

Extraction

The chelating, agent EDTA was used for extraction of Aloe pectin from the cell wall fibers. The fibers were suspended in water at 0.2–2% (w/v). The EDTA stock solution was prepared at 0.5 M and a pH of 7.0 or 8.0 and added to the fiber suspension. The final concentration of EDTA used was 25 mM. The final pH of the fiber suspensions was adjusted with NaOH to the indicated values. The extraction was done with stirring at either RT or with high temperature ("HT") of about 80° C., or in a sequential manner—RT extraction followed by HT extraction. HT was carried out up to 80° C. and then stopped before the separation step. In the sequential extraction, the remaining fibers following the RT extraction were re-suspended to the same volume in water without washing and fresh EDTA was added at the same concentration as for the RT extraction. Following extraction, remaining fibers were removed by centrifugation (500 g, 15 min) or by filtering with a no. 18 sieve followed by gauze sponge filtering. The gauze sponges (4×4, 8 ply) were used with three pieces together and set up in a disc filter frame. The sponges were washed with water before use. The gauze sponge filtration was highly efficient in removing the residual small fibers after the sieve filtration. When necessary, the extract was passed through the sponge filter twice. The filtrate was essentially clear. For quantitative studies on yields from sequential extraction, fibers were always removed by centrifugation following the first round of extraction at RT. Alcohol (ethanol) was added to the clear supernatant or filtrate to a final concentration of 75% (v/v). The precipitates were collected by centrifugation (500 g, 15 min) or with the no. 18 sieve and washed twice with 75% alcohol. The alcohol wash step was necessary to remove residual EDTA The precipitates were then pressed to remove alcohol, dried, and stored at BUT before use.

The extraction of Aloe pectins with the chelating agent EDTA was found to be highly efficient and a yield as high as 50% (w/w) could be obtained. The pectins obtained had an average galacturonic acid content above 70 % (w/w). The pH was found to have a major effect on the pectin yield with EDTA extraction. A 5 mg/ml fiber suspension in water had a pH of ~3.7 (34). The pH of the fiber suspension was 7.7 (7.5–8.0) following addition of pH 8.0 EDTA stock to a final concentration of 25 mM. A pH of 6.4 (6.3–6.5) was obtained when a pH 7.0 EDTA stock solution was used to give a final concentration of 25 mM The pH 5.0 was obtained by using a pH 5.0 sodium acetate buffer at a final concentration of 20 mM, a common condition for pectin extraction. It was found that there was no major difference in yield following RT extraction at a pH from 5.0 to 7.7. A major effect of pH, however, was found during HT extraction. A yield increase by >20% was noted at pH 7.7 as compared to pH 5.0 or pH 6.4 during HT extraction of fresh fibers. Furthermore, a nearly 2-fold increase in yield was noted when the remaining fibers from the first round of RT extraction were extracted under HI with fresh pH 8.0 EDTA added as compared to using pH 7.0 EDTA. The pH values of the fiber suspensions did not change significantly at the end of RT extraction. However, after re-suspending in water and addition of fresh EDTA, the pH (~8.5) of the suspensions was actually higher than that of EDTA stock solutions (pH 8.0). It was further found using the fresh fibers under HT extraction that the pH 8.5 extraction did give a much higher yield, more than 2-fold higher than that at pH 5.0 and ~40% higher than that at pH 7.7. Increasing the pH to 90. however did not improve the yield much further (<10%) as compared to pH 8.5. Ensuing experiments also showed that a substantial increase (20%) in yield was also obtained with RT extraction at pH 8.5.

RT was less efficient than HT during extraction. The yield was similar between these two conditions provided the RT extraction was extended in time. The yield by RT extraction approached the maximum by ~4 hrs. Further extension of the extraction time did not significantly improve the yield. The yield of the second extraction with HT varied depending on the length of the first RT extraction; therefore the yield with HT would be higher if RT extraction was performed for only 1 hr, or lower when the RT extraction was performed for 4 hrs or longer.

Repeated extraction under the same conditions produced a progressively lower yield. The yield decreased by approximately half with each extraction. The remaining fibers can therefore be suspended in half the volume from the previous extraction.

EDTA and fiber concentrations also influenced the extraction efficiency. When 25 mM EDTA was used with a 2 mg/ml fiber suspension, yield between 50–60% could be obtained with a single extraction under HT. When using a 5 mg/ml fiber suspension with the same EDTA concentration, the yield decreased to ~30% With the sequential room temperature to high temperature extraction a combined yield of 40–50% could be readily obtained. No difference in yield was noted between alcohol treated and non-alcohol-treated fibers.

Other chelating agents were also considered for Aloe pectin extraction Ammonium oxalate was not used because it is considered a toxic agent. Using sodium hexametaphosphate, a considerable yield was obtained; however, this agent was difficult to remove because of precipitate formation in alcohol solution and an acid (HCl or $HNO_3$) precipitation step was required before the alcohol wash.

Other conditions were also examined for Aloe pectin extraction. Hot dilute acid and cold alkaline solutions are two other common conditions for pectin extraction. Both of them can cause extensive degradation. Commercial pectins from citrus and apple were extracted under the hot dilute acid condition. Using this condition for the Aloe pectin, the pH of fiber suspensions was adjusted to 1.5 with HCl followed by HT up to 80° C. The yield obtained is much lower compared to using EDTA extraction. The extraction by HT in water alone yielded virtually no alcohol precipitable materials. Renault and Thibault (Renault and Thibault, *Carbohyrate Research,* 1993, 244, pp. 99–114) reported that extraction of apple and sugar beet fibers in PBS (PH 6.5) with HT (80° C.) generated a high yield similar to that by EDTA extraction. Using this condition, only a low yield was obtained from the Aloe Vera pulp fibers. Cold alkaline extraction was performed with 50 mM NaOH or 50 mM $Na_2CO_3$ at 4° C. The pH in suspension was 11.5 with 50 mM NaOH and 10.5 with 50 mM $Na_2CO_3$. After 1 hr at 4° C., a very low yield was obtained with 50 mM $Na_2CO_3$. No alcohol precipitable materials were obtained with 50 mM NaOH. When the extraction was done at RT for 1 hr, no yield was obtained with either agent, suggesting that pectins are rapidly degraded under these conditions.

Together, these results showed that extraction with EDTA at pH 7.0–8.5 is the most efficient extraction method for Aloe pectin. With the sequential RT to HT extraction, a high yield (40–50%, w/w) could be obtained along with production of both HMW and LMW Aloe pectins. The uniqueness of this extraction procedure was the higher pH (7.0–8.5) used. The reason behind this higher pH is that Aloe pectins are naturally LM (see below) which are more resistant to β-elimination under alkaline conditions and EDTA functions most efficiently at a pH above 7.0. In addition, EDTA is more soluble at a pH above 7.0 and can therefore be more readily removed during alcohol precipitation and wash steps.

The green rind fibers produced a similar yield of pectin compared to the pulp fibers when extracted with the pH 8.0 EDTA. This rind pectin was equally rich in Gal A. The amount of fibers obtained from the rind was more than 10 times higher than that from the pulp (per unit of leaves). This is consistent with the fact that the rinds consisted much smaller cells as compared to the pulp. Together, these results indicated that a very large amount of Aloe pectin can be obtained from the rind portion of the leaf, which is currently discarded as waste materials by some manufacturers.

To extract LM/HMW Aloe pectins with EDTA at about room temperature, the workable pH range appeared to be between about 5 and about 8.5, preferably about 8–8.5. To extract LM/LMW Aloe pectin with EDTA at elevated temperature (for example at about 80° C.), the workable pH ranges appeared to be between about 5 and about 8.5, preferably about 8.0. At pH of higher than 6.5, EDTA extraction of HM pectins from other sources at elevated temperature would lead to the degradation of the products. For the extraction of pectins from other plant sources using EDTA or other chelating agents, the reported pH ranges are 4–6.5.

EXAMPLE 2

Pectin Purification by Ion Exchange Chromatography

The ion exchange chromatography was performed on a Pharmacia Biotech AKTA explorer chromatography system. The column was three Pharmacia Hi-trap Q, 5 ml cartridges connected in series. Aloe pectins were dissolved in water at 1 mg/ml and loaded onto the column at a flow rate of 1 nil/min After washing with 15 ml of water, bound materials were eluted with a linear gradient of NaCl (0–1.0 ) The column eluant was monitored by UV absorbance at 215, 254, and 280 nm. Fractions containing pectin formed precipitates which were collected by low speed centrifugation, pooled, and redissolved in water. They were then desalted by passing through a Sephadex G-25 column. The pectin-containing fractions were collected, dried, and stored at room temperature.

EXAMPLE 3

Calcium Gel Formation

Aloe pectins at various concentrations in water were mixed with calcium chloride solution at various concentrations along with commercial LM and HM pectins. After standing at RT for up to 24 hrs, the tubes were inverted. If the sample flowed easily, it was considered that no gel formation occurred. If the sample did not flow or deform under its own weight, gel formation had occurred. If the sample did not flow, but deformed (i.e., the surface did not keep a straight line perpendicular to the side of the tube when tubes were held at a horizontal position), the system was considered as a soft gel. The results showed that Aloe pectin obtained by either RT or HT extraction from either pulp or rind fibers formed firm gels in the presence of calcium as did the LM citrus pectin and polygalacturonic acid. Under the same conditions, the HN citrus pectin did not form gels. This is consistent with the fact that the Aloe pectin is a LM pectin. Pectins from citrus and apple are naturally HM pectins. LM pectins are obtained by demethylating the EBM pectins. Since no harsh conditions were applied during the extraction of Aloe pectins, especially with RT extraction, the Aloe pectin is a natural LM pectin.

With a 0.2% Aloe pecan solution, the minimum concentration of calcium chloride required for gel formation was determined to be 1–2 mM (50–100 mg $CaCl_2$/g pectin). A gel could also be obtained using $ZnCl_2$ at a similar concentration. With increasing concentrations of pectin and/or calcium chloride, the gel became gradually firmer. It was noted that the HMW Aloe pectins formed gels more readily than LMW Aloe pectins in that it took less time for gel formation and the gel seemed firmer.

Increasing the ionic strength facilitated the calcium gel formation. The speed of gel formation gradually increased with increasing NaCl concentrations (0–0.2 M) after the addition of a fixed amount of calcium chloride.

EXAMPLE 4

Monovalent Cation-Based Gel Formation

Aloe pectins were dissolved in water at various concentrations. The pectin solutions were mixed at RT with equal volumes of 0.3 M NaCl (2×saline), 0.3 M NaCl and 40 mM sodium acetate (pH 5.0), or 2×PBS (pH 7.4). The final volumes were 1 or 2 ml. The tubes (12×75 mm) were then placed in a fridge at 4° C. or on ice (0° C.). The gel formation was judged as described in Example 3. The tubes were then returned to RT to determine if the gel reverted back to solution. Various NaCl concentrations (0.05–1 M) were tested for gel formation. The potassium salt (KCl) was also tested. The salt and pectin solutions were always mixed in equal volumes (1:1). For determining the effect of endo-polygalacturonase on the gel formation, pH 5.0 acetate buffer was added to pectin solutions to a final concentration of 20 mM. The enzyme was then added at indicated concentrations. After standing at RT for 30 min the solutions were mixed with equal volumes of 0.3 M NaCl and then placed on ice. The gel formation was examined as above.

When an Aloe pectin solution in 0.15 M NaCl (physiological saline) was cooled to 4° C., a gel was obtained. The gel was firm and free standing when kept at 4° C. just as the calcium gel; it turned quickly back to solution when brought to RT (22° C.). This reversible solution-gel transition could be repeated many times by changing the temperature.

Unlike the gel formation in the presence of calcium which occurred efficiently with both HMW and LMW Aloe pectins, the monovalent cation-based gel formation only occurred efficiently with HMW Aloe pectins obtained from either pulp or rind fibers. The sample AP 97-1 and similar ones, which had molecular weights of >1×10$^6$ Da, could produce firm gels at concentrations as low as 1 mg/ml in the presence of 0.15 M NaCl. Such gels were also clear when the pectin concentrations were 5 mg/ml or less. With higher pectin concentrations (>5 mg/ml), gels were firmer and slightly cloudy. With a 1 ml volume, a gel could form in ~15 min after the tube was placed on ice and returned to solution in about the same time after it was brought back to RT. The gel, however, did not revert back to solution at a temperature as high as 15° C. The gel could form at pH 5.0 (in saline with 20 mM pH 5.0 sodium acetate) as well as pH 7.4 (in PBS).

The LMW (0.375–6.08×10$^5$ Da) Aloe pet only formed such gels at higher concentrations ($\geq$5 mg/ml). At 1 mg/ml only soft gels could be obtained with some of the LMW samples in 0.15 M NaCl. The smallest Aloe pectin sample (0.375×10$^5$ Da) formed no gel at 1 mg/ml in 0.15 M NaCl. A soft gel was only obtained with this sample at a pectin concentration of 10 mg/ml in 0.2 M NaCl. This suggests that the efficiency of the monovalent cation-based gel formation is dependent on the size of the pectin molecules. Aloe pectin could be degraded by endo-polygalacturonase. Thus, 300 μl of 2 mg/ml AP97-1 pectin solution in 20 mM pH 5.0 sodium acetate was digested with this enzyme at various concentrations before mixing with an equal volume of 0.3 M NaCl and placed on ice. The results showed that the control (no enzyme added) formed a gel and the sample with the highest enzyme concentration remained a solution. Between the control and the highest enzyme concentration, the transition from solution to gel was evident, i.e., the gel became softer with an increase in the enzyme concentration until a complete solution was obtained at the highest enzyme concentration. This result indicates that the size of the Aloe pectin molecules is an important factor in monovalent cation-based gel formation.

The gel formation was also dependent on the NaCl concentration. In 0.1 M NaCl, only soft gels were obtained with samples like AP 97-1. The firm gels only formed in 0.15 M and 0.2 M NaCl. Whereas the gel formed at 0.15 M NaCl was fully reversible when the gel was brought back to RT, the gel formed at 0.2 M NaCl was not readily reversible, especially for the HMW Aloe pectins. This gel formed with NaCl is referred to as pectin sodium gel. After standing at RT for 1 hr or longer, syneresis often occurred with the gel formed at 0.2 M NaCl, i.e., the liquid was separated from the gel. With higher NaCl concentrations ($\geq$0.4 M), precipitates formed at RT. The precipitates were white and amorphous at high NaCl concentrations (0.6–1 M) and appeared to be fine granules at 0.4 M NaCl.

Such cold gelation is also sensitive to the species of monovalent cations used. With KCl (0.05–1 ), no cold gel formation occurred, although precipitates were formed at higher KCl concentrations ($\geq$0.4 M) at RT.

Precipitation of pectins at high salt concentrations and RT has been previously observed. However, such a reversible monovalent cation (NaCl)-based cold gelation under the physiological condition (0.15 M NaCl, pH 7.4) has not previously been described with any other pectins. So far, no such gelling system has been identified with any other polymers or substances in literature. Using the commercial polygalacturonic acid, LM and HM pectins, no such monovalent cold gelation was obtained.

EXAMPLE 5

Growth Factor Binding by Pectin

Generically, a heparin-binding growth factor ("HBGF") is mixed with a pectin in a solution of water, buffer, or saline to give the resultant pectin/heparin-binding growth factor ("PHBGF"). The mixture can be stored at a temperature range of between about –80° C. and about 37° C., preferably between about –80° C. and about 22° C., and more preferably between about –80° C. and about 4° C. Alternatively, the mixture can be lyophilized and stored at the same temperature ranges. The concentration or amount of pectin in the mixture can range from about 0.001 mg/ml to about 40 mg/ml, preferably from about 0.01 mg/ml to about 20 mg/ml, and more preferable from about 0.05 mg/ml to about 10 mg/ml The concentration or amount of HBGH in the mixture can range from about 0.01 ng/ml to about 500,000 ng/ml, and preferably from about 0.1 ng/ml to about 250,000 ng/ml, and more preferably from about 1 ng/ml to about 100,000 ng/ml.

EXAMPLE 6

Growth Factor Binding by Aloe Pectin

Pectin-rich cell wall fibers were isolated from BAM or from homogenized fresh Aloe Vera inner gel. BAM was suspended in deionized water at 2 mg/ml. The solutions were stirred at room temperature ("RT") for 3 hrs or at 4° C. overnight. They were then centrifuged at low speed (1000 rpm or 180 g) for 10 min (Beckman TJ-6). The pellet or cell wall fiber was collected, washed once with deionized water, and dried (Centrivap, Labconco). For isolation of cell wall fibers from fresh inner gel, Aloe Vera leaves were cleaned by washing with water and filleted to remove the outer green rind. The clear inner gel was homogenized and cell wall fibers were isolated by centrifugation at 500 g for 15 min. They were washed once with 75% alcohol and then three times with deionized water. The isolated cell wall fibers were then further homogenized to ensure they were small enough (~200 μm) so that they could be handled in a consistent manner through pipette tips. They were then dried before use. These fibers were rich in Aloe pectin (~50%, w/w). They were used in the binding assay and also for pectin extraction. Cell wall fibers were also isolated from the fresh rind in the same manner and used for pectin extraction.

Aloe pectin was extracted from the inner gel or rind cell wall fibers as described in Example 1. Briefly, the extraction was performed with the chelating agent (EDTA) either at RT or with heating (80° C.) and at a pH of 7.5–8.5. Pectin was precipitated with ethanol (75%, final concentration) and washed twice with 75% ethanol. It was dried and stored at RT. Extraction at RT produced the high-molecular-weight (HMW; $0.785–1.36 \times 10^6$ Da) Aloe pectin and the heating extraction produced the low-molecular-weight (LMW; $0.375–6.08 \times 10^5$ Da) one.

For binding assays, proteins were dissolved in TN buffer (25 mM Tris, 0.15 M NaCl, pH 7.4) at 100 μg/ml. Proteins (1 μg) were mixed with 20 μg of the inner gel cell wall fibers in a 200 μl reaction volume. BSA (20 μg), which was shown to be a non-binding protein, was also added to the reaction mixture to prevent non-specific binding. The mixtures were gently vortexed and incubated at 37° C. for 1 hr with gentle vortexing once every 20 min. The cell wall fibers were then pelleted at 500 g for 5 min and washed three times with TN buffer. They were then suspended in gel loading buffer and kept in a boiling water bath for 3 min before separation by SDS-polyacrylamide gel electrophoresis. A 15% gel was used. The protein bands were visualized by Coomassie blue staining. For densitometry analysis of the protein bands, the Coomassie blue-stained gel images were acquired using GS-5000 digital imaging system (Alpha Infotech Co.) and the optical densities (OD) of protein bands were measured using the NIH image program (version 1.6; National Institute of Health). A positive binding was identified by detection of the protein band from the binding reaction with an OD value at least 2 times higher than that of the control (i.e. protein alone).

For inhibition assays, various amounts of soluble Aloe pectin or heparin prepared in TN buffer were added to the binding reaction. The rest of the steps were carried out as described above.

Figure 1A:
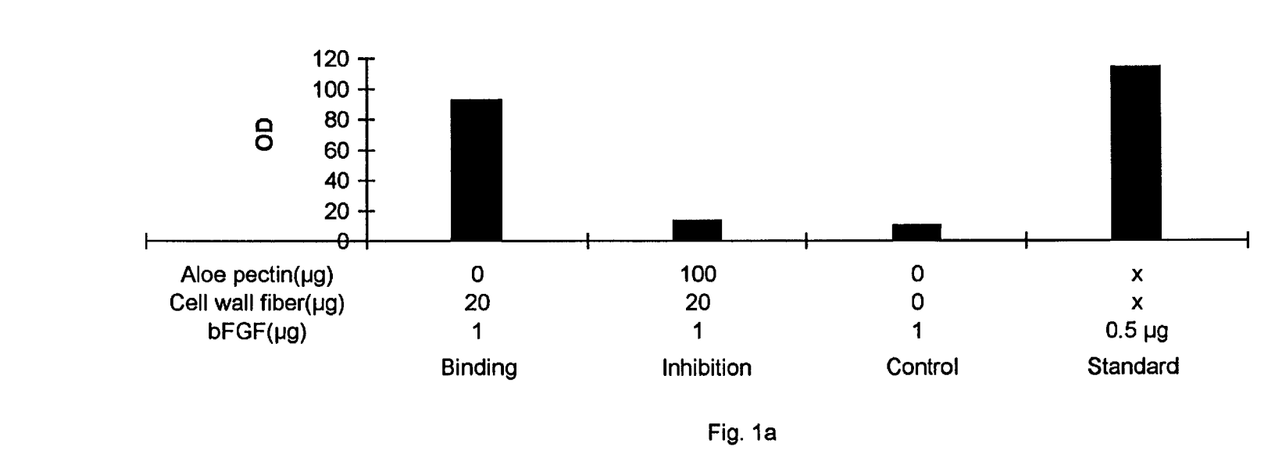
Figure 1B:
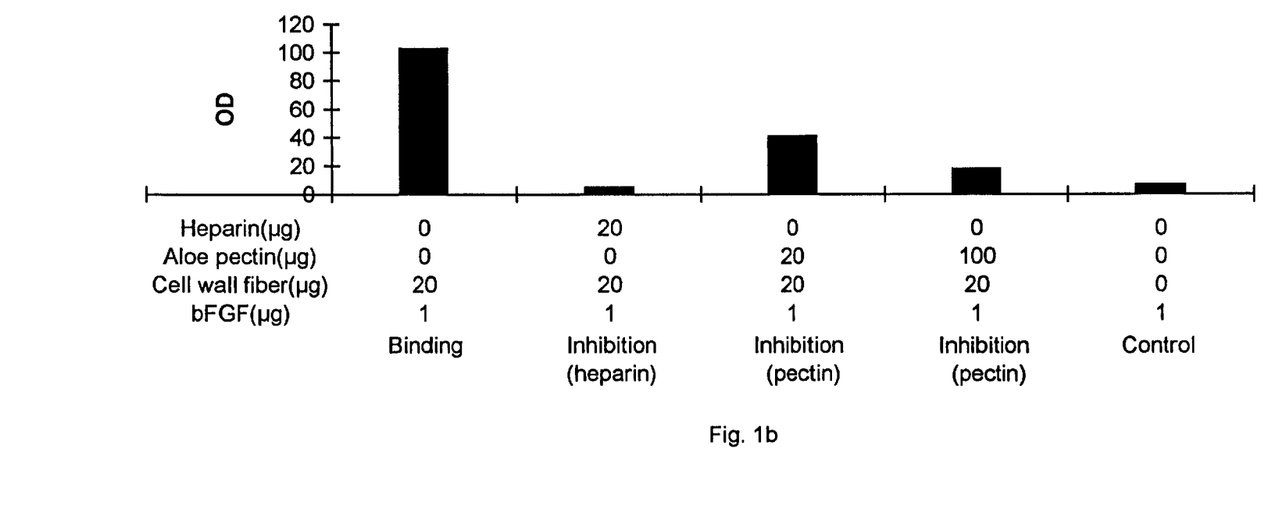

The results showed that Aloe pectin bound tom aFGF, bFGF, KGF, and TGF-β1, but not to Il-8, Il-1β, IFN-γ, EGF, TGF-α, TNF-α, PDGF, C3, fibronectin or BSA (Table 1) aFGF, bFGF, and KGF belong to FGF family and TGF-β1 belongs to TGF-β family. Members of these two growth factor families are all heparin-binding. aFGF, bFGF, and KGF and TGF-β1 are some examples of the pectin/heparin-binding growth factors. Thus, these results showed that Aloe pectin bound to the heparin-binding growth factors. The binding to the heparin-binding proteins tested (Il-8, IFN-γ, and fibronectin). However, no binding was detected with any of non-heparin-binding proteins tested (IL-1β, EGF, TGF-α, TNF-α, PDGF, C3, or BSA). The binding to bFGF and KGF was particularly strong since ~0.5 μg out of the 1 μg protein used was bound under the experimental conditions used. The results with bFGF are shown in FIG. 1. The binding was effectively inhibited by soluble Aloe pectin. Both LMW and HMW Aloe pectins from either inner gel or outer rind inhibited the binding. This confirmed that the binding to the pectin-rich cell wall fibers was mediated by the pectin molecules (FIG. 1). The binding was also inhibited by heparin (FIG. 1), being consistent with the heparin-binding nature of these growth factors.

EXAMPLE 7

Growth Factor Binding by Other Pectins

Various commercial pectins were used in the inhibition assay to determine if they have similar binding activities. The included de-esterified pectin (i.e. polygalacturonic acid) prepared from citrus pectin, citrus LM pectin (DM, 28%), and citrus HM pectins with a DM of 64% or 92%. All of them produced cloudy solutions when dissolved. Before use, they were centrifuged at 25,000 g for 30 min to remove the insoluble materials. The soluble pectins were precipitated with ethanol (75%, final concentration) and washed once with 75% ethanol. They were then dried and stored at room temperature.

Figure 2:
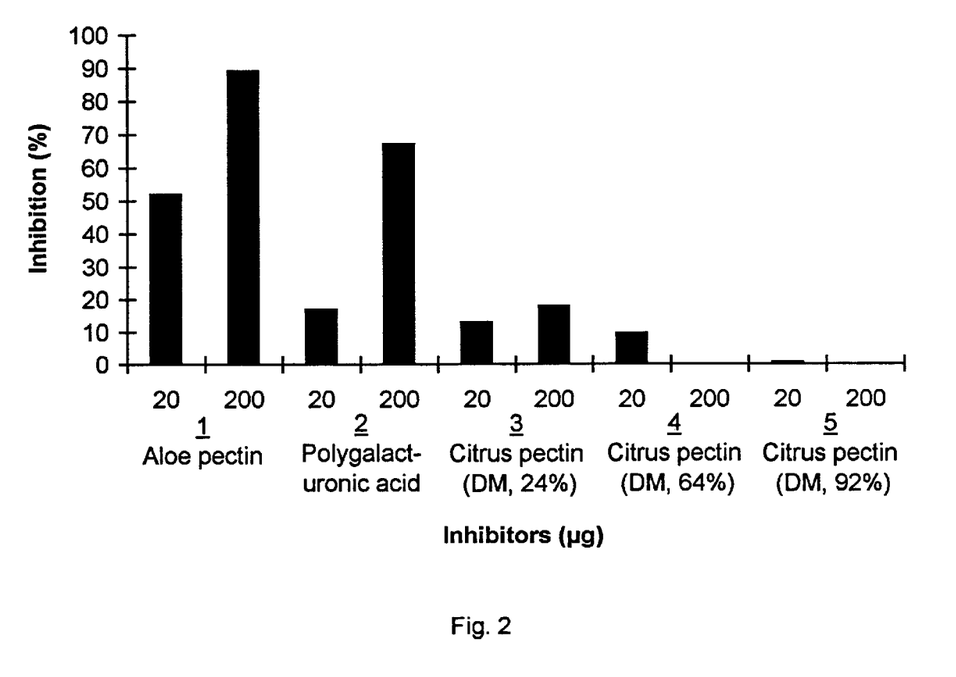
FIG. 2. shows a comparison of Aloe pectin with other pectins of various DM values in inhibiting the binding of bFGF to the pectin-rich Aloe Vera inner gel cell wall fibers.

The inhibition assays were carried out with bFGF as described above. Aloe pectin exhibited an inhibition of 52% at 20 μg and 89% at 200 μg (FIG. 2). No inhibition (<20%) was observed with LM (DM, 28%) or HM (DM, 64%, or 92%) pectins at either 20 or 200 μg (FIG. 2), indicating that these pectins do not bind to the growth factor. A weak inhibition, however, was observed with the polygalacturonic acid as compared to Aloe pectin, i.e., no inhibition (<20%) was observed at 20 μg, but a significant inhibition (67%) was observed at 200 μg (FIG. 2). This indicates that polygalacturonic acid can also bind to the growth factor although not as strongly as the Aloe pectin.

EXAMPLE 8

Protection of Growth Factor Against Protease Digestion

Heparin binding has been shown to stabilize growth factors against inactivation by proteases. To determine if the pectin binding confers any protective effect on the growth factors, bFGF was subjected to trypsin digestion in the presence or absence of Aloe pectin or inner gel cell wall fibers. bFGF (0.5 μg) was mixed with Aloe pectin or inner gel cell wall fibers (0–16 μg) in a 15 μl reaction volume and incubated at 37° C. for 10 min followed by the addition of trypsin (0.5 μg). The mixtures were incubated at 37° C. for 1 hr and then mixed with the gel loading buffer and subjected to electrophoresis as described above.

Figure 3:
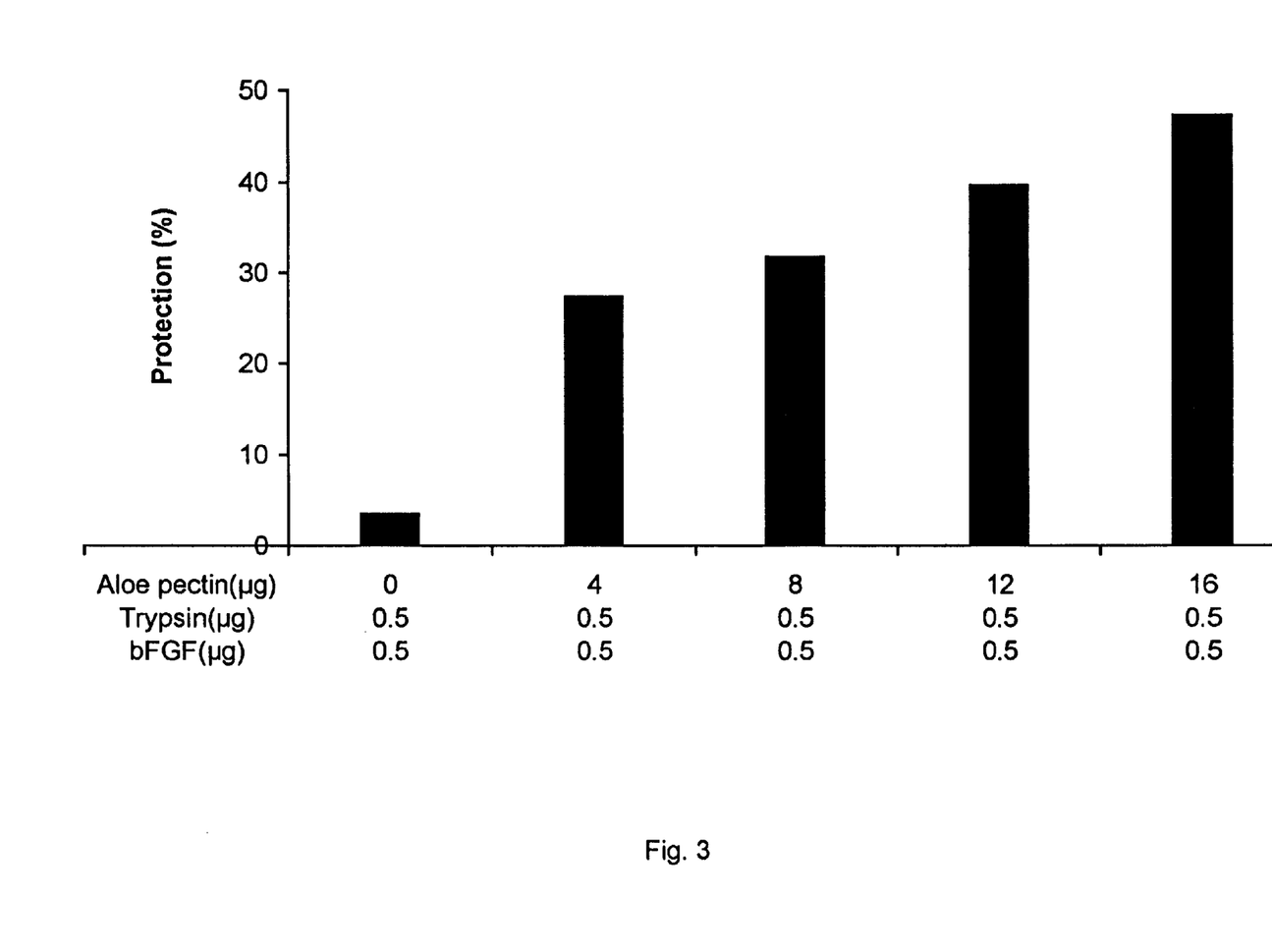
FIG. 3. shows the protection of bFGF by Aloe pectin against enzyme digestion. bFGF (0.5 µg) was mixed with trypsin (0.5 µg) in the presence or absence of Aloe pectin as described in Example 8. Following incubation at 37° C. for 1 hr, bFGF was separated by SDS-polyacrylamide gel electrophoresis.

The results showed that under the conditions used, bFGF (0.5 μg) was almost completely digested by trypsin in the absence of Aloe pectin, i.e., only 3.5% of bFGF was still intact (FIG. 3). However, in the presence of Aloe pectin, the bFGF was protected in a dose-dependent manner. A 27, 32, 40, or 47% protection (remaining/starting×100%) was obtained with 4, 8, 12, or 16 μg of Aloe pectin (FIG. 3). When BSA, a non-binding protein, was used instead of bFGF, no such protection effect was observed. This indicates that binding by Aloe pectin does confer a stabilizing effect on the growth factor. The same dose-dependent protection of bFGF against trypsin digestion was also observed with inner gel cell wall fibers.

The protection by polygalacturonic acid was weaker as compared to Aloe pectin, i.e., the amount of bFGF protected by polygalacturonic acid was much less than that by Aloe pectin at any given amount used.

EXAMPLE 9

Growth Factor Binding by Pectin Calcium Gel Beads

In stabilizing a pectin/heparin-binding growth factor ("PHBGH") with a calcium gel bead, the PHBGH is mixed with pectin calcium gel beads suspended in a buffered or non-buffered solution. The mixture is shaken at between about 0° C. and about 37° C., preferably between about 0° C. and about 30° C., and more preferably between 4° C. and about 22° C., for a period of from 5 minutes to about 24 hours, preferably from about 15 minutes to about 6 hours, and more preferably between about 30 minutes to about 2 hours. The treated beads are then isolated, and stored in a solution. Alternatively, the beads are dried by lyophilization. The concentration or amount of PHBGH that can be used in the mixture can range from about 0.1 ng/ml to about 500,00 ng/ml, preferably from about 1 ng/ml to about 100,000 ng/ml. The concentration or amount of the pectin for the making of gel beads ranges from about 1 mg/ml to about 40 mg/ml, preferably from about 5 mg/ml to about 30 mg/ml, and more preferably from about 10 mg/ml to about 20 mg/ml. The size of the pectin calcium gel beads used in the mixture can vary from about 3–mm to about 10 μm, depending on the dripping method used. The resultant treated beads can be stored in a temperature range of between about −80° C. and about 37° C., preferably between about −20° C. and about 22° C., and more preferably between about 0° C. and about 4° C.

Aloe pectin, like other LM pectin, is capable of forming a gel in the presence of calcium ($CaCl_2$). The Aloe pectin calcium gel beads were prepared by dripping the Aloe pectin solution (10 mg/ml) into a 200 mM $CaCl_2$ solution under stirring. Depending on the dripping mechanism, bead size could vary from about 3–4 mm to <10 μm. Dripping through a syringe needle gives larger beads, whereas spraying with a fine sprayer produces smaller beads. The beads formed in this experiment were ~1 mm in diameter. These beads were then used in the binding assay as described in Example 6 except that the binding reaction mixtures were kept at room temperature with constant shaking for 1 hr.

Figure 4:
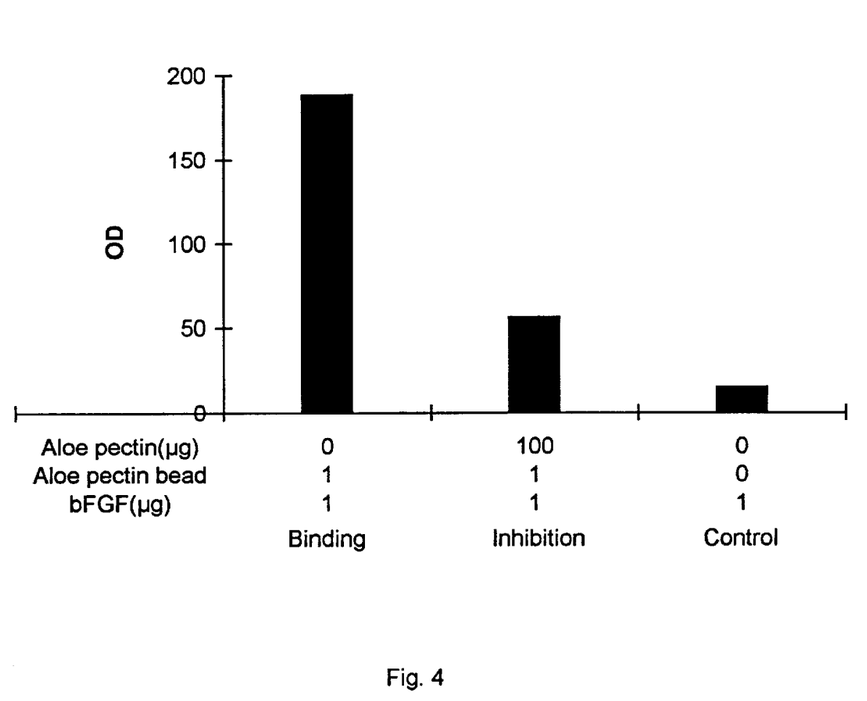
FIG. 4. shows the binding of Aloe pectin calcium gel beads to bFGF. The binding assay was carried out as described in Example 9. One gel bead was used for each binding assay. Soluble Aloe pectin was used as an inhibitor.

The results showed that these beads bound to bFGF (FIG. 4). The binding was inhibited by the soluble Aloe pectin. The same result was also obtained with KGF. This suggests that such beads can be loaded with the growth factor. Thus, pectin beads prepared with Aloe pectin can be used as a delivery vehicle for the PHBGH.

EXAMPLE 10

Encapsulation of Growth Factors in Pectin Calcium Gel and Monovalent Cation-Based Gel Generically, in stabilizing a pectin/heparin-binding growth factor ("PHBGF") with a monovalent cation-based gel, such as an Aloe pectin sodium gel, the PHBGF is mixed with a pectin, such as an Aloe pectin, in a buffered or non-buffered physiological saline (about 0.15 M NaCl). The mixture is kept at between about 0° C. and about 4° C. so that the monovalent cation-based gel can form. The concentration or amount of PHBGF that can be used in the mixture is as described in Example 5. The concentration or amount of the pectin that can be used in the mixture ranges from about 0.1 mg/ml to about 20 mg/ml, preferably from about 0.5 mg/ml to about 10 mg/ml, and more preferably from about 1 mg/ml to about 5 mg/ml. The resultant mixture can be stored in a temperature range of between about −80° C. and about 37° C., preferably between about −20° C. and about 22° C., and more preferably between about 0° C. and about 4° C.

Generally, in stabilizing a PHBGF with pectin calcium gel, the PHBGF is mixed with a pectin, such as an Aloe pectin, in a solution of calcium salt of from about 0.1 mM to about 500 mM, preferably from about 0.5 mM to about 100 mM, and more preferably from about 1 mM to about 20 mM. Alternatively, the mixture of pectin and PHBGF was dripped into a 200 mM $CaCl_2$ bath to form beads as described in Example 9. The concentration or amount of PHBGF that can be used in the mixture is as described in Example 5. The concentration or amount of the pectin that can be used in the mixture ranges from about 0.1 mg/ml to about 40 mg/ml, preferably from about 0.5 mg/ml to about 30 mg/ml, and more preferably from about 1 mg/ml to about 20 mg/ml. The resultant mixture can be stored in a temperature range of between about −80° C. and about 37° C., preferably between about −20° C. and about 22° C., and more preferably between about 0° C. and about 4° C.

Aloe pectin solution in deionized water or physiological saline (0.15M NaCl) was mixed with bFGF so that the final pectin concentration was 10 mg/ml and the final bFGF concentration was 100 μg/ml. The mixtures were then dripped into a 200 mM $CaCl_2$ solution to make the calcium gel beads.

The beads were readily formed in the presence of bFGF. Using bovine serum albumin ("BSA"), beads could be obtained at a BSA concentration of 10 mg/ml. The beads could also be obtained by dripping the BSA-containing pectin solution into a 200 mM $ZnCl_2$ solution. Such gel bead formation was also achieved with the de-esterified citrus pectin (polygalacturonic acid), although a higher concentration (20 mg/ml) of polygalacturonic acid had to be used. Growth factors/cytokines are generally used at a concentration well below 100 μg/ml. Thus, the protein concentration is not a limting factor for preparing such calcium gel beads. Compared to loading the pre-formed pectin beads with growth factors described in Example 9, entrapment in calcium gel likely provides a more protective delivery device since growth factors are entrapped inside the gel matrix. This form of delivery device is more suitable for oral use.

For monovalent cation-based gel formation, the pectin and bFGF mixture was prepared in physiological saline (0.15 M NaCl) with a HMW Aloe pectin at a concentration of 1–2 mg/ml. The bFGF concentration was the same as above (100 μg/ml). A gel formed after the mixture was kept at 0–4° C. for 10–30 min dependent on the volume of the mixture. Using BSA, such a gel could be obtained at a BSA concentration of 20 mg/ml. Thus, these pectin/heparin-binding growth factors can be stored in a gel. This not only provides a direct stabilizing effect but also reduces the chance for aggregate formation. The gel was reversible, changing quickly back to solution when brought back to room temperature (22° C.) and thus allowing the agent to be used in solution form.

EXAMPLE 11

Affinity Chromatography with Inner Gel Cell Wall Fiber as a Pectin-Containing Matrix To assess the binding strength between Aloe pectin and the growth factors, affinity chromatography was performed with inner gel cell wall fiber as a pectin-containing matrix. Inner gel cell wall fibers (0.4 ml) were packed into a 5 ml-column. The column was washed extensively with TN buffer. The bFGF (8 $\mu$g in 200 $\mu$l) was loaded onto the column, which was then washed with 8 ml TN buffer at a flow rate of 6 ml/hr. The elution was performed stepwise with 0.4 ml each of 0.15, 0.2, 0.3, 0.4, 0.5, 0.6, 0.7, 0.8, 0.9, 1.0, and 2.0 M NaCl. The eluate was then analyzed by gel electrophoresis to detect bFGF as described above.

Figure 5:
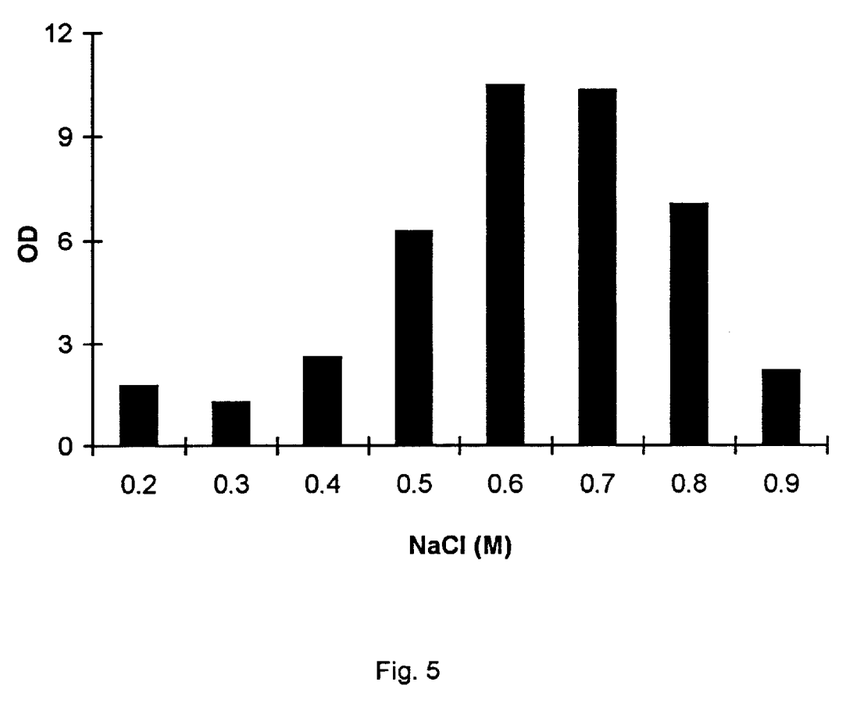
FIG. 5. shows the affinity chromatography w Aloe Vera inner gel cell wall fiber as a pectin-containing matrix. bFG-F was loaded onto a column consisting of inner gel cell wall fibers. Elution was performed stepwise with 0.4 ml of NaCl at various molar concentrations. Fractions were subjected to gel electrophoresis for detection of bFGF.

The results showed that bFGF was eluted at 0.5–0.7 M NaCl with the peak at 0.6 M (FIG. 5). This showed that the binding strength of bFGF to Aloe pectin was moderate and weaker than that to heparin; bFGF is eluted from a heparin column at 1.4–1.6 M NaCl and aFGF at 0.8–1.0 M NaCl (0.3–0.4 M NaCl is considered weak binding and >1.0 M NaCl is considered strong binding; Conrade, (1998), Heparin-binding Proteins, Academic Press, San Diego, pp. 197–199).

The weaker affinity to Aloe pectin as compared to heparin most likely makes it more suitable for using Aloe pectin as a stabilizer and delivery vehicle, i.e., once the growth factor bound to Aloe pectin contacts the glycosaminoglycan (heparin) on the cell surfaces, it will bind to the latter, its natural higher-affinity ligand for initiating a stimulatory effect on cells.

EXAMPLE 12

Coupling of Pectin to a Support for Isolation of Pectin/Heparin-Binding Proteins The carboxyl group of the Gal A residue in pectin is used for coupling of pectin to an amine-contain support with a carbodimide compound EDC (1-ethyl-3-(3-dimethylaminopropyl)-carbodiimide). The amine-containing support can be the commercially available aminohexylsepharose (Amersham Pharmacia Biotech) or diaminodipropylamine immobilized on 3M Emphaze support (Pierce, Rockford, Ill.). Pectin (1–20 mg/ml) is prepared in a buffer (0.1 M Mes, 0.15M NaCl, pH 4.7) and mixed with the matrix. The EDC (0.1–20 mg/ml) is added to initiate the coupling which lasts for 3 hrs at RT under shaking. After being washed with 1 M NaCl, the matrix is ready for use.

EXAMPLE 13

Pharmaceutical Formulation of Pectin/Heparin-Binding Growth Factor

One embodiment of a pharmaceutical formulation of a pectin/heparin-binding growth factor can be made by mixing and blending the following ingredients:

A pectic substance in a amount ranging from about 0.001 mg/ml to about 40 mg/ml;

A pectin/heparin-binding growth factor ("PHBGF") in an amount ranging from about 0.1 ng/ml to about 100,000 ng/ml. The PHBGF can be selected from the group consisting of an acidic fibroblast growth factor a basic fibroblast growth factor, a keratinocyte growth factor and a transforming growth factor $\beta 1$;

A thickener in an amount ranging from about 20 mg/ml to about 150 mg/ml. The thickener can be selected from the group consisting of a hydroxyethyl cellulose, a Karaya gum, a cationic polyacrylamide compound, and a sodium carboxyl methyl cellulose;

An optional preservative in an amount ranging from about 0.02 mg/ml to about 5 mg/ml. The optional preservative can be selected from the group consisting of a paraben, a benzothonium halide, a benzoic acid, a benzoate, a sorbic acid, a sorbate, a sodium borate, and an antibiotic.

An optional dispersant in an amount ranging from about 10 mg/ml to about 150 mg/ml. The optional dispersant can be selected from the group consisting of PVP, vinyl acetate copolymer, and polyvinylpyrrolidone.

The remaining is water, saline or a buffer solution.

Although the invention has been described with reference to the presently-preferred embodiments, it should be understood that various modifications can be made without departing from the spirit of the invention. Accordingly, the invention is limited only by the following claims.

What is claimed is:

1. A method of isolating a pectin/heparin-binding protein, comprising:

preparing a pectin-containing matrix comprising a pectic substance and a matrix;

bringing into contact a mixture containing the pectin/heparin-binding protein with the pectin-containing matrix; and subsequently isolating the pectin/heparin-binding protein.

2. The method of claim 1, wherein the pectin substance is de-esterified pectin, a low-methoxyl pectin, a pectin calcium gel, an Aloe pectin sodium gel, a pectic acid, a pectate, or a mixture thereof.

3. The method of claim 1, wherein the pectin/heparin-binding protein comprises a pectin/heparin-binding growth factor.

4. The method of claim 1, wherein the pectin-containing matrix comprises a pectin substance coupled to an agarose or sepharose bead, a pectin calcium gel bead, or an Aloe Vera inner gel cell wall fiber.

* * * * *